United States Patent [19]

Johnson et al.

[11] Patent Number: 5,264,570
[45] Date of Patent: Nov. 23, 1993

[54] METHOD FOR MAKING 2-[$^{18}$F]FLUORO-2-DEOXY-D-GLUCOSE

[75] Inventors: Bruce F. Johnson, Scotia; Donald H. Maylotte, Schenectady; Cheryl L. Sabourin, Albany, all of N.Y.

[73] Assignee: General Electric Company, Schenectady, N.Y.

[21] Appl. No.: 925,063

[22] Filed: Aug. 5, 1992

[51] Int. Cl.$^5$ .................... C08B 37/00; C07H 1/00
[52] U.S. Cl. ............................ 536/122; 536/18.4; 536/18.5; 536/124
[58] Field of Search ................ 536/122, 124, 18.4, 536/18.5

[56] References Cited

U.S. PATENT DOCUMENTS 4,794,178  12/1988  Coenen et al. ............... 536/122
5,169,942  12/1992  Johnson et al. ............. 536/122

OTHER PUBLICATIONS

Abstract—Removal of the 2.2.2 cryptand (Kryptofix 2.2.2) from fluorine—18 labeled 2-deoxy-2-[$^{18}$F]-fluoro-D-glucose, DL Alexoff et al Appl. Radiat. Isot., 42(12), 1189–93 (1991).

Article—Effects of Reaction Conditions on Rates Incorporation of No-Carrier Added F-18 Fluoride into Several Organic Compounds, ML Korguth et al—1988 by John Wiley & Sons, Ltd. pp. 360–381.

Article—Efficient Stereospecific Synthesis of No-Carrier-Added 2-[$^{18}$F]Fluor-2-Deoxy-D-Glucose Using Aminopolyether Supported Nucleophilic Substitution, K Hamacher et al—J. Nucl Med. 27:235–238 (1986).

Article—Recommendation for a Practical Production of [2-$^{18}$F]Fluror-2-Deoxy-D-Glucose, H. H. Coenen et al—Appl. Radial. Isot. vol. 38, No. 8 pp. 605–610 (1987).

Article—Robotic Production of 2-Deoxy-2[$^{18}$F]-Fluror-D-Glucose: A Routine Method of Synthesis Using Tetrabutylammonium [$^{18}$F]Fluoride—J. W. Brodack et al—Appl. Radial. Isot. vol. 39, No. 7, pp. 699–703 (1988).

Article—Routine Production of 2-Deoxy-2[$^{18}$F]-Fluoro-D-Glucose by Direct Nucleophilic Exchange on a Quaternary 4-Aminopyridinium Resin, S. A. Toorongian et al.—Nucl. Med Biol. vol. 17, No. 3 pp. 273–279 (1989).

*Primary Examiner*—Ronald W. Griffin
*Attorney, Agent, or Firm*—William A. Teoli; William H. Pittman

[57] ABSTRACT

A method is provided for synthesizing 2-fluoro-2-deoxy-D-glucose having an [$^{18}$F] fluoride ion employing a dibenzo substituted aminopolyether (Kryptofix 222BB) as a phase-transfer reagent.

3 Claims, No Drawings

METHOD FOR MAKING 2-[$^{18}$F]FLUORO-2-DEOXY-D-GLUCOSE

CROSS REFERENCE TO RELATED APPLICATIONS

Reference is made to copending application Ser. No. 07/795,575, filed Nov. 21, 1991, Pat. No. 5,169,942.

BACKGROUND OF THE INVENTION

The present invention relates to a method for synthesizing 2-fluoro-2-deoxy-D-glucose with an [$^{18}$F]fluoride ion prepared without addition of a carrier to produce a radiopharmaceutical for Positron Emission Tomography (PET). More particularly, the present invention relates to a method for making 2-[$^{18}$F]fluoro-2-deoxy-D-glucose involving the replacement of the trifluoromethanesulfonyl group (triflate) with an [$^{18}$F]fluoride ion in 1,3,4,6-tetra-O-acetyl-2-triflate-$\beta$-D-mannopyranose, where a phase-transfer reagent (PTR) is used in the form of a dibenzo substituted aminopolyether alkali metal complex (Kryptofix 222BB).

Prior to the present invention, various procedures were used for making 2-[$^{18}$F]fluoro-2-deoxy-D-glucose or "[$^{18}$F]2FDG", which is the most widely used radiopharmaceutical for Positron Emission Tomography (PET). Considerable effort has been expended in the development and refinement of such procedures. Because of its decay energy, (0.64 MEV) the [$^{18}$F] fluoride ion allows the highest inherent resolution during PET measurements and has a relatively convenient half life of 109.7 min. The following equation illustrates the preferred procedure for making [$^{18}$F]2FDG:

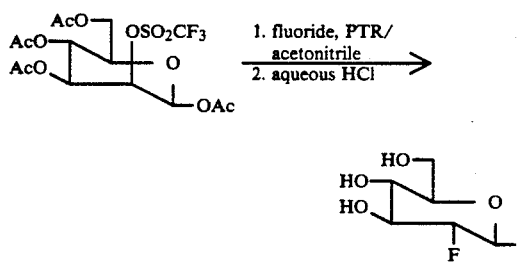

where AcO is acetate.

One method of synthesizing [$^{18}$F]2FDG by the above procedure is shown by Hamacher et al., Journal of Nuclear Medicine, 27:235-238, (1986). Hamacher et al. employ an aminopolyether [Kryptofix 222 or "K222"]-potassium carbonate complex as a phase-transfer reagent for [$^{18}$F]fluoride. An additional procedure for making [$^{18}$F]2FDG is shown by Brodack et al., Applied Radiation and Isotope, Volume 39, No. 7, pages 699–703 (1988) involving the employment of a tetrabutylammonium hydroxide as a phase-transfer reagent in place of the aminopolyether potassium complex of Hamacher et al.

Although cryptands, such as Kryptofix 222 having the formula,

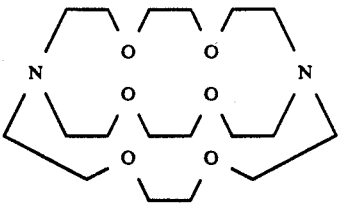

have been found useful as phase transfer reagents, cryptands also have been found to be toxic. As a result their use in producing radiopharmaceuticals for PET applications has to be carefully monitored to assure their absence in the final product. Means for enhancing the detection and removal of cryptands from the product stream are therefore constantly being sought.

SUMMARY OF THE INVENTION

The present invention is based on the discovery that a dibenzo substituted cryptand, (Kryptofix 222BB) having the formula,

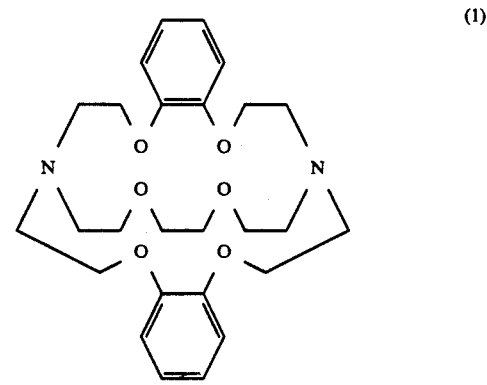

(1)

is substantially equivalent to Kryptofix K222 as a PTR and can be readily detected quantitatively using a single beam spectrophotometer, or using HPLC/UV techniques. In addition, during standard recovery of [$^{18}$F]2FDG, using C18 Sep-pak to effect decolorization and removal of hydrophobic impurities, Kryptofix 222BB is substantially removed, while significant amounts of Kyrptofix K222 have been found in the final [$^{18}$F]2FDG product. As a result a significant advance in the synthesis of [$^{18}$F]2FDG has been made.

STATEMENT OF THE INVENTION

There is provided by the present invention, a method for making 2-[$^{18}$F]fluoro-2-deoxy-D-glucose which comprises, (1) contacting at a temperature of 40° C. to 100° C., 1,3,4,6-tetra-0-acetyl-2-0-trifluoromethanesulfonyl-2-deoxy-$\beta$-D-mannopyranose and [$^{18}$F]fluoride ion in the presence of an inert organic solvent and the phase-transfer reagent of formula (1), (2) effecting the substantial removal of the organic solvent, (3) heating the resulting mixture of (2) in the presence of an aqueous hydrogen halide until deprotection of the resulting acetylated 2-[$^{18}$F]fluoro-2-deoxy-D-glucose is effected, and (4) recovering 2-fluoro-2-deoxy-D-glucose from the mixture of (3).

In the practice of the invention, Kryptofix BB, hereinafter referred to as "the phase-transfer reagent" or "PTR" and an alkali metal carbonate, such as potassium carbonate, is dissolved in an aqueous organic solvent such as acetonitrile or propronitrile. There can be used from about 2.5 to 3 millimoles of the PTR and about 1 to 3 millimoles of the alkali metal carbonate per 100 ml of organic solvent. There is added to the resulting solution, an aqueous organic solvent solution containing the [$^{18}$F] ion from a cyclotron target. The resulting solution can be evaporated to dryness at temperatures preferably in the range of from 50° C. to 70° C. under a partial vacuum with an inert gas, such as helium. Additional organic solvent, such as acetonitrile can be added and the evaporation procedure continued. To the resulting mixture, there can be added a solution of the 1,3,4,6-tetra-0-acetyl-2-triflate-$\beta$-D-mannopyranose, referred to hereinafter as "triflate". The triflate can be used in a proportion of 0.03 millimole to 0.1 millimole, per 100 ml of organic solvent. The resulting mixture can then be heated under reflux conditions for a period of from 4 to 10 minutes. The mixture can then be evaporated to dryness and the resulting product hydrolyzed with aqueous HCl by heating the resulting mixture for a period of about 15 to 20 minutes under reflux conditions. Upon completion of the hydrolysis, the solution can then be passed through a chain of columns. Initially the mixture can be passed through Dowex 50W resin in the H+ form which consists of sulfonic acid functionalized polystyrene to effect the removal of the phase-transfer reagent. In addition, the mixture can be passed through an ion retardation resin (Biorad AG 11A8) of the Bio-Rad Lab Inc. of Rockville Center, N.Y., to effect neutralization. Additional impurities such as color and hydrophobic impurities can be removed with C18 Sep-pak of the Waters Co of Milford, Mass., while a neutral alumina Sep-pak (Waters) can be used to remove any remaining fluoride ion. An alternative chain of columns consisting of sulfonic acid functionalized silica (Bakerbond spe) of the J. T. Baker Company of Phillipsburg, N.J., can be used to remove the phase-transfer reagent and quarternary amine functionalized silica (Bakerbond) for neutralization.

In order that those skilled in the art will be better able to practice the present invention, the following example is given by way of illustration and not by way of limitation. All parts are by weight.

EXAMPLE

There was added 3 ml of acetonitrile and water containing $^{18}$F ion from a cyclotron target to a solution of 80-90 $\mu$moles of phase-transfer reagent (K222BB) and 40-50 $\mu$moles of potassium carbonate dissolved in 1 ml of an 80/20 acetonitrile/water mixture. The resulting solution was then evaporated to dryness at 60°-70° C. under a partial vacuum of helium gas. An additional 5 ml of acetonitrile was added and the evaporation procedure was repeated. A solution of 80 $\mu$moles of 1,3,4,6-tetra-O-acetyl-2-triflate-$\beta$-D-mannopyranose and 4 ml of acetonitrile was added to the reaction vessel and the reaction vessel placed in a 95°-105° C. oil bath for 8 minutes during which time the reaction vessel contents refluxed. The resulting solution was then evaporated to dryness. The hydrolysis of the [$^{18}$F]fluoride ion substituted triflate was achieved by adding 2 ml of 2N HCl and heating the reaction vessel in a 115°-125° C. oil bath for 20 minutes, during which time the contents of the reaction vessel refluxed. After hydrolysis, the solution was passed through a chain of columns consisting of sulfonic acid functionalized polystyrene (Dowex 50W resin in the H+ form) to remove the K222BB, followed by passage through an ion retardation resin (Biorad AG11A8) to neutralize the product mixture, followed by C18 Sep-pak (Waters) to remove color and hydrophobic impurities and a neutral alumina Sep-pak (Waters) to remove any remaining fluoride ion. A yield of 74%±10% of [$^{18}$F]2FDG was obtained. A similar procedure utilizing Kryptofix 222 as shown by Hamacher et al. provided a yield of 58%-80%.

In addition to satisfactory yields, the recovered [$^{18}$F]2FDG made by the method of the present invention using Kryptofix K222BB was compared to the method of the prior art using Kryptofix K222 with respect to residual traces of the phase-transfer reagent in the final [$^{18}$F]2FDG product. The following procedure using TLC and HPLC techniques was employed.

A series of columns was used to analyze the [$^{18}$F]2FDG product prepared above to determine the wt % of phase transfer reagent present, if any. There was initially used an ion retardion column (AG11A8) of the Bio-Rad Lab, Inc. of Rockville Center, N.Y. The product was then analyzed to determine the wt % of PTR. The product was then passed through a series of columns consisting of ion retardation (AG11A8) Biorad, C18 Sepak K reverse phase column (Waters Co of Milford, Mass.) and a Sepak R, neutral alumina column. The product was analyzed again to determine the presence of PTR.

Using the above procedure, it was found that Kryptofix K222 was present at 30-50% by weight of the initial charge. The Kryptofix K222BB was found to be present at 5-7%.

In addition, a further sample of the [$^{18}$F]2FDG product after recovery was treated with a sulfonic acid derivative of a silica gel made by J. T. Baker Co before being analyzed by the above procedure. It was found that the [$^{18}$F]2FDG was found to be free of both Kryptofix K222BB and Kryptofix K222PTR.

The above results show that [$^{18}$F]2FDG made by the method of the present invention using K222BB can be recovered substantially free of, or at a lower wt % level of toxic cryptands as compared to [$^{18}$F]2FDG made using Kryptofix K222 as a phase-transfer reagent. In addition, when solutions of the [$^{18}$F]2FDG made by the above procedures were analyzed with a single beam spectrophotometer for traces of cryptands, Kryptofix K222BB was more easily detected as compared to Kryptofix K222.

Although the above example is directed to only a few of the very many variables which can be employed in the practice of the method of the present invention, it should be understood that the present invention is directed for the use of organic solvents and conditions as set forth in the description proceeding this example.

What is claimed is:

1. A method for making 2-[$^{18}$F]fluoro-2-deoxy-D-glucose which comprises,
    (1) contacting at a temperature of 40° C. to 100° C., 1,3,4,6-tetra-O-acetyl-2-0-trifluoromethanesulfonyl-2-deoxy-$\beta$-D-mannopyranose and [$^{18}$F]fluoride ion in the presence of an inert organic solvent and the phase-transfer having the formula,

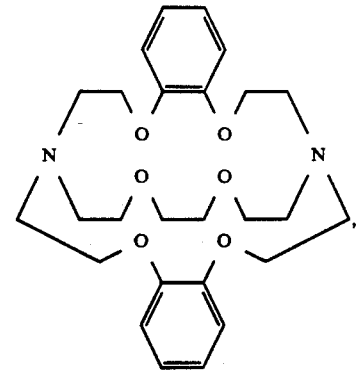

(2) effecting the substantial removal of the organic solvent, (3) heating the resulting mixture of (2) in the presence of an aqueous hydrogen halide until deprotection of the resulting acetylated 2-[$^{18}$F]fluoro-2-deoxy-D-glucose is effected, and (4) recovering 2-[$^{18}$F]fluoro-2-deoxy-D-glucose from the mixture of (3).

2. A method in accordance with claim 1, where the organic solvent is acetonitrile.

3. A method in accordance with claim 1, where the 2-[$^{18}$F]fluoro-2-deoxy-D-glucose is recovered using a derivatized silica gel column followed by a reverse phase column to effect removal of cryptands.

* * * * *